United States Patent [19]  
Duprez et al.

[11] 4,233,186  
[45] Nov. 11, 1980

[54] CATALYSTS FOR WATER DEALKYLATION OF AROMATIC HYDROCARBONS

[75] Inventors: Daniel Duprez, Poitiers; Michel Grand, Serezin du Rhone, both of France

[73] Assignee: Elf Union, Paris, France

[21] Appl. No.: 21,193

[22] Filed: Mar. 16, 1979

[30] Foreign Application Priority Data

Mar. 20, 1978 [FR] France ............................... 78 07987

[51] Int. Cl.³ ........................ B01J 21/04; B01J 23/40; B01J 23/70; B01J 23/72
[52] U.S. Cl. ............................. 252/466 B; 252/466 J; 252/466 PT
[58] Field of Search .......... 252/466 PT, 466 J, 466 B; 585/487; 423/600

[56] References Cited

U.S. PATENT DOCUMENTS

| | | | |
|---|---|---|---|
| 2,436,923 | 3/1948 | Haensel | 252/459 X |
| 3,691,247 | 9/1972 | Billings | 585/487 |
| 3,823,088 | 7/1974 | Box et al. | 252/463 X |
| 4,013,734 | 3/1977 | Kim | 585/487 |

FOREIGN PATENT DOCUMENTS 1542505  4/1972  Fed. Rep. of Germany ....... 252/466 B

*Primary Examiner*—W. J. Shine  
*Attorney, Agent, or Firm*—Burgess, Ryan and Wayne

[57] ABSTRACT

Water dealkylation catalysts of petroleum fractions containing monoalkylated or polyalkylated aromatic hydrocarbons including at least one metal of group VIII deposited in a proportion of from 0.1 to 5% by weight on a spinel, and having deposited in a proportion of from 0.1 to 5% by weight on a spinel, and having improved properties of activity, selectivity and stability, characterized in that the carrier is a mixed spinel of the formula $(M_xM'_{1-x})Al_2O_4$ wherein M is a bivalent base metal of group VIII such as nickel, iron and cobalt and M' is a bivalent metal belonging to groups 2a, 7b, 1b or 2b such as magnesium, manganese, copper and zinc.

The mol. ratio M/M' may vary from 0.5:1 to 50:1, preferably from 1:1 to 20:1.

13 Claims, No Drawings

CATALYSTS FOR WATER DEALKYLATION OF AROMATIC HYDROCARBONS

This invention concerns itself with a water catalytic dealkylation process of monoalkylated or polyalkylated aromatic hydrocarbons, characterized by the use of a specific catalyst including at least one metal of group VIII deposited on a carrier composed of a mixed spinel according to a particular method of preparation.

To satisfy the demand of benzene, it is necessary to dealkylate a portion of the aromatic alkyl hydrocarbons. The treatment with water vapor makes it possible to carry out said dealkylation while producing a considerable amount of hydrogen.

Several processes of water dealkylation that use catalysts having a base of metals of group VIII are known. Haensel, U.S. Pat. No. 2,436,923, first described such as process in 1948; the catalyst claimed includes Co, Ni, Ru, Rh, Pd, Os, Ir and Pt. In French Pat. No. 1,588,876 and patents corresponding thereto, Rabinovich-Maslyanskii claimed a catalyst containing a noble metal of group VIII, specifically rhodium, deposited on alumina either pure or coated with nickel or cobalt. A Japanese team of the firm Mitsubishi claimed the improvement of the performances of rhodium by coating the alumina carrier with cerium or uranium. French Pat. No. 2,169,875 to UOP described a catalyst having a base of rhodium on a chromium-alumina oxide coated with iron or potassium (U.S. Pat. No. 3,436,433. Girdler German Pat. No. 2,357,496 likewise described a water process where alumina is advantageously replaced by chromium oxide.

Recently, Exxon (U.S. Pat. No. 4,013,734) claimed the improvement of Rh catalysts on alumina by coating the alumina with vanadium.

CFR described improved performances of rhodium deposited on alumina of low acidity by associating the rhodium with tin.

It seems in effect, on the one hand, that rhodium is one of the most active metals for the process, but that on the other hand, the carrier of the catalyst plays an important part in the performances of the catalyst.

The present invention is based on the discovery of particularly interesting performances of supported metallic catalysts containing at least one metal of group VIII deposited on a carrier composed of a mixed spinel of the formula $M,M'_{1-x}Al_2O_4$, M being a bivalent metal of group VIII specifically chosen from metals such as iron, nickel and cobalt and M' being a bivalent metal of group 2a, 7b, 1b or 2b, preferably magnesium, manganese, copper or zinc, the ratio M/M' varying between 0.5:1 and 5:1 preferably between 1:1 and 20:1 These catalysts make it possible to obtain an elevated activity in the reaction involving dealkylation of the aromatics associated with a good selectivity and an entirely remarkable stability; said catalysts functioning for as long as 400 hours without any modification of the conditions of operation. The dealkylation is carried out within a temperature range of from 400° to 600° C., preferably from 420° to 550° C., under a pressure of from 0 to 80 bars, preferably from 0 to 60 bars.

The hourly spatial speed of the hydrocarbons based on the feeding is from 0.1 to 10 $h^{-1}$, preferably from 0.3 to 4 $h^{-1}$. The molar ratio between the water and the hydrocarbon at the feed level is from 2 to 20, preferably from 4 to 10.

The spinels are mixed oxides of the general formula $AB_2O_4$ wherein A is a bivalent metal and B is a trivalent metal. In certain cases, much rarer, A can be a tetravalent metal and B a bivalent metal. These are compounds of cubic crystalline structure in which the oxygen ions form a compact cubic stack.

The metallic ions can occupy two types of sites; the tetrahedral sites wherein the metallic ion is surrounded by 4 oxygen ions and the octahedral sites wherein the metal is surrounded by 8 oxygen ions. The respective positions of A and B allows to differentiate the normal spinels and the inverse spinels. The spinels can be prepared by a dry or by a wet method. In the dry method, an equimolar mixture of the two oxides AO and $B_2O_3$ is brought to an elevated temperature in the presence of a melting agent, generally boric acid. In the wet method, a co-precipitate is made of the hydroxides A $(OH)_2$ and B $(OH)_3$ that is then calcined at an elevated temperature.

For the aluminum spinels M $Al_2O_4$, the temperatures generally recommended for the calcining are from 900° to 1100° C. Relatively recent studies (see in particular A. M. Rubinstein, Kin. I Katal 1967, 8 (No. 5) 1094) have shown that certain mixtures of oxides such as NiO and $Al_2O_3$ reorganize starting from 300° C., and the recrystallization to spinel takes place starting at 700° C. Therefore, the transformation to spinel is very quick between 900° C. and 1100° C.

A complete description of the spinels, of their structure and of the mode of preparation thereof is given in "The New Treatise of Mineral Chemistry" by P. Pascal, Masson Ed (1961), Volume VI, page 596. "Inorganic Chemistry" by R. B. Heslop and P. L. Robinson, 3rd ed. Elsevier P. Co. 1967, page 207 describes the structure of the spinels and French Pat. No. 2,086,903 and U.S. Pat. No. 3,791,992 describe certain methods of preparation.

In accordance with the invention, the mixed spinels that serve as carriers are prepared by bringing to an elevated temperature, mixtures of MO, $Al_2O_3+M'O$, M and M' being two bivalent metals. There are thus obtained mixed spinels $(M_xM'_{1-x}) Al_2O_4$ wherein x is the molar fraction of M. The carriers thus prepared are charged with one or several active metals selected from group VIII of the periodic table such as rhodium, platinum, palladium, iridium and mixtures thereof. Iridium, rhodium or a mixture thereof is preferably used in a proportion of from 0.1 to 5% by weight, the relative proportions of the noble metals of group VIII thus deposited varying from 1/10 to 10/1.

The metals are introduced by dry impregnation or moist impregnation with an aqueous or acid solution of the salt of the metal selected. In the dry impregnation, the volume of solution is exactly equal to the volume of retention to saturation of the carrier. After such an impregnation, the solution is entirely absorbed. In the moist impregnation, an excess of solution is used. The metal is then adsorbed from said solution. To obtain a total adsorption, it is possible to evaporate the solution slowly.

After introducing the metal or metals desired, the catalyst is dried and then calcined in air. Prior to the reaction, it is reduced by a current of hydrogen at a temperature of from 400° to 550° C. After the reduction, the catalyst is treated with water vapor at a temperature of from 400° to 600° C. for a period of time of from 5 minutes to 15 hours, preferably from ¼ to 4 hours.

To illustrate the invention without limiting it, the following examples applied to the dealkylation of toluene are given.

EXAMPLE 1

A catalyst having 0.6% by weight of rhodium deposited on a mixed spinel $Ni_{0.5}Mg_{0.5}Al_2O_4$ is prepared as follows: 258 g aluminum nitrate Al $(NO_3)_3$. 9 $H_2O$ (theoretical molecular weight 375.1 g), 50 g nickel nitrate Ni $(HO_3)_2$. 6 $H_2O$ (theoretical molecular weight 290.8) and 43 g magnesium nitrate Mg $(NO_3)_2$. 3 $H_2O$ (theoretical molecular weight 255.4 g) are dissolved together in 500 cm³ exchanged water, while stirring.

The dissolution being endothermic, the solution is restored to room temperature by slightly heating for two hours. The metallic hydroxides are then precipitated as follows: while stirring very strongly, concentrated ammonia 22° Baume is added until the appearance of the first flakes of hydroxides that can no more be dissolved. The precipitation by ammonia 2 N is terminated at a pH 6.5. Care must be taken not to exceed said pH since re-dissolution can occur by ammoniated complexes of part of the metals, especially nickel, which results in the appearance of a dark blue solution.

The coprecipitate is filtered on a Buchner funnel under vacuum. The coprecipitate is dried at 160° C. under vacuum for 36 hours, then washed, while recovering it by 500 cm³ exchanged water. It is again filtered, then dried at 160° C. under vacuum for 48 hours. It is calcined by bringing it to 200° C. for 1 hour, to 400° C. for 1 hour, and then to 600° C. for 2 hours, A grey-black solid is then obtained. The transformation to spinel is effected by calcining the carrier at 900° C. for 3 hours and then 1000° C. for 15 hours. It is then cooled in a desiccator. The solid has then a light blue color intermediate between that of the Ni $Al_2O_4$ spinel that is of a darker blue and that of the Mg $Al_2O_4$ spinel that is white. 56.5 g of solid is recovered, that is, more than 98% of the theoretical yield. 0.55 g hydrated rhodium chloride is dissolved (with 39–40% rhodium) in 15 cm³ acetic acid 0.1 N. 35 g mixed spinel (Mg, Ni) $Al_2O_4$ are immersed in this solution. It is constantly stirred for 5 minutes and allowed to stand in the air for 1 hour. The volume of solution is calculated in a manner such that all the liquid is absorbed. The catalyst is then dried at 140° C. for 4 hours, then calcined in two stages; for ½ hour by progressively increasing the temperature to 200° C., then for ½ hour at 500° C. The catalyst is then cooled in the desiccator.

20 g of the catalyst thus prepared are put in a fixed-bed dynamic reactor for testing under the following conditions: temperature of the bed: 438° C.: pressure=6 bars (5 relative bars); VVH of the toluene (volume of toluene per unit of volume of catalyst and per hour) equal to 0.9, molar ratio $H_2O$/toluene=8; at the end of 23 hours of operation, the molar yield of benzene in relation to toluene passed is 0.66; it is 0.81 in relation to the converted toluene.

EXAMPLES II to IV

The examples that follow are given by way of indication for comparing the performances of the catalysts of this invention with catalysts including rhodium deposited on simple spinels of the type M $Al_2O_4$ or M $Cr_2O_4$ or M $Rh_2O_4$ (in this last case, the rhodium is directly included in the spinel).

The tests are carried out at a pressure of 2 bars, the temperature of the catalytic bed is 465° C., the v.v.h is 0.9, the molar ratio $H_2O$/TOLUENE is 8.0. The results are reported in Table I.

Catalyst No. 2 is unquestionably the most active of the rhodium catalysts deposited on simple spinel; it has been tested for 200 h for appraising the stability (Table II). The test is carried out under the following conditions. Temperature: 450° C., vvh=0.90; molar ratio $H_2O$/TOLUENE=8; pressure: 2 bars. Catalyst No. 2 has a good activity and quite a good stability, but its selectivity is not very good.

EXAMPLE VII

Catalyst No. 1 is tested under the conditions of Example I (438° C.; vvh=0.9; $H_2O$/TOLUENE=8) under different pressures. The results are given in Table III.

The activity of catalyst No. 1, according to the invention, is substantially th same as that of the 0.6% Rh catalyst on simple spinel Ni $Al_2O_4$. On the other hand, its selectivity and particularly its stability, are clearly improved. At 6 bars, for example, from 9 h to 360 h without modifying the operating parameters, no deactivation is observed.

EXAMPLE VIII

A catalyst is prepared having 0.6% Rh deposited on mixed spinel $Ni_{0.75}$ $Mg_{0.25}$ $Al_2O_4$ (catalyst No. 6) in conformity with Example I while adjusting the amounts of nickel and magnesium salts so as to satisfy the stoichiometric ratio Ni/Mg=3 (for 258 g aluminum nitrate: 75 g nickel nitrate and 21.5 g magnesium nitrate). Ten grams of the catalyst thus prepared are tested at 442° C., 2 bars, vvh=0.90 and a molar ratio $H_2O$/toluene—8. The test results are given in Table IV. Catalyst No. 6 according to the instant invention has a particularly elevated activity with very good selectivity. The stability is also quite remarkable.

EXAMPLE IX

For appraising the behavior of catalyst No. 6 in conditions of industrial operation where the determining factors are: sufficient stability and the most elevated possible selectivity, said catalyst has been tested at 396° C. (Table V).

This table sets forth the excellent selectivity of catalyst No. 6 for rates of conversion between 40 and 50%. This selectivity is essentially limited by the appearance in the products of considerable amounts of xylenes (0.8 to 2% in the hydrocarbonated liquid phase).

EXAMPLES IX TO XV

The examples that follow are given for appraising the behavior of catalyst No. 6 in different conditions of operation. (Table VI).

EXAMPLES XVII TO XIX

Bimetallic catalysts containing 0.5% rhodium and 0.1% of another metal of group VIII deposited o a mixed spinel of nickel, magnesium and aluminum are prepared following the procedure of Example VIII by adjusting the amounts of the metal salts for the impregnation. The carrier chosen is the one of Example VIII with a ratio Ni/Mg=3. The results are given in Table VII.

The bimetallics Rh Pt, Rh Pd and Rh Ir have interesting selectivities; among said bimetallics, the rhodium-iridium catalysts are the most stable.

EXAMPLE XX

In the spinels Ni Al$_2$O$_4$, the substitution of magnesium for part of the nickel results in catalysts of absolutely remarkable properties for the water dealkylation of aromatics. The examples that follow make it possible to appraise the good properties of catalysts with rhodium deposited on mixed spinel Ni$_x$M'$_{1-x}$Al$_2$O$_4$ wherein M' is a bivalent metal of groups 7b, 1b and 2b. The carriers are prepared following the procedure of Example I, substituting for the magnesium salt the stoichiometric amount of the salt of the metal M'. The results are given in Table VIII.

TABLE I

| EX. | CATALYST NO. | DESCRIPTION | 2 h Conversion | 2 h Selectivity | 6 h Conversion | 6 h Selectivity | 25 h Conversion | 25 h Selectivity |
|---|---|---|---|---|---|---|---|---|
| II | 2 | 0.6% Rh on Ni Al$_2$O$_4$ | 93.7% | 76% | 91.0% | 80.5% | 84.7% | 82.0% |
| III | 3 | 0.6% Rh on Mg Al$_2$O$_4$ | 49.0% | 87.3% | 49.0% | 87.0% | 48% | 87.5% |
| IV | 4 | 0.6% Rh on Cu Al$_2$O$_4$ | 32.5% | 92.9% | 32.4% | 92.9% | 31.8% | 93.1% |
| V | 5* | Ni Rh$_2$O$_4$ on gamma alumina at 0.6% by weight of rhodium | 25.4% | 85.5% | 21.8% | 87.1% | 19.4% | 87.8% |

*This catalyst is prepared by impregnating the gamma alumina with the necessary amount of nickel and rhodium salt so that Ni/Rh = 0.5 and the rhodium content of the catalyst is 0.6% by weight. The catalyst is then calcined at elevated temperature (900 then 1000° C.) like in Example I.

TABLE II

| Catalyst and Test Conditions | TIME (Hours) | CONVERSION | SELECTIVITY | Yield of Benzene (For 1 mol. Toluene Passed) |
|---|---|---|---|---|
| 0.6% Rh on Ni Al$_2$O$_4$ (n° 2) | | | | |
| 450° C. | 2 h | 90% | 72% | 0.648 |
| 2 bars | 6 h | 88% | 73% | 0.642 |
| VVh = 0.90 | 24 h | 84% | 76% | 0.638 |
| with 10 g of catalyst | | | | |
| $\frac{H_2O}{TOLUENE} = 8$ | 200 h | 73% | 77.5% | 0.566 |
| +10° C. (460° C.) | 210 h | 79% | 74% | 0.585 |

TABLE III

| Catalyst And Test Conditions | TIME (HOURS) | P = 2 bars Conversion | P = 2 bars Selectivity | P = 6 bars Conversion | P = 6 bars Selectivity | P = 41 bars Conversion | P = 41 bars Selectivity |
|---|---|---|---|---|---|---|---|
| No. 1 (0.6% Rh on mixed spinel) | 6 h | 80% | 76% | 85.5% | 78% | 80% | 79% |
| Ni$_{0.5}$Mg$_{0.5}$Al$_2$O$_4$ | 24 h | 75% | 80% | 81.5% | 81% | 79% | 80% |
| 438° C. | 50 h | 71% | 82% | 76.5% | 82% | 78% | 81% |
| vvh = 0.9 | 90 h | 70% | 83% | 73.5% | 83% | 81% | |
| with 10g catalyst | 200 h | 69% | 84% | 73.5% | 83% | 78% | 81% |
| $\frac{H_2O}{TOLUENE} = 8$ | 360 h | | | 73.5% | 83% | | |

TABLE IV

| Catalyst And Test Conditions | TIME | CONVERSION | SELECTIVITY |
|---|---|---|---|
| No. 6 (0.6% Rh on mixed spinel | 6 h | 95.6% | 77% |
| Ni$_{0.75}$ Mg$_{0.25}$Al$_2$O$_4$) | 24 h | 93.5% | 81.5% |
| 442° C. | 50 h | 92.7% | 82.5% |
| with 10 g catalyst | 100 h | 91.5% | 82.8% |
| H$_2$O/TOLUENE = 8 | 150 h | 89.5% | 84.0% |
| 2 bars | 200 h | 88.5% | 84.2% |

TABLE V

| Catalyst And Test Conditions | HOURS | CONVERSION | SELECTIVITY |
|---|---|---|---|
| No. 6 | 6 h | 50.8% | 91.5% |
| 396° C. | 24 h | 47.3% | 93.5% |
| vvh = 0.90 | | | |
| $\frac{H_2O}{TOLUENE} = 8$ | 50 h | 44.9% | 95.7% |
| 2 bars | 200 h | 41.2% | 96.0% |

TABLE VI

| EXAMPLE NO. | Temperature | Pressure | VVH | H$_2$O/TOLUENE | TIME (HOURS) | CONVERSION % | SELECTIVITY % |
|---|---|---|---|---|---|---|---|
| IX (rap.) | 396° C. | 2 bars | 0.90 | 8 | 50 h | 44.9% | 95.7% |
| X | 405° C. | 2 bars | 0.90 | 8 | 50 h | 50.9% | 91.0% |
| XI | 426° C. | 2 bars | 0.90 | 8 | 50 h | 70.9% | 89.0% |

TABLE VI-continued

| EXAMPLE NO. | TEST CONDITIONS | | | | TIME (HOURS) | CONVERSION % | SELECTIVITY % |
|---|---|---|---|---|---|---|---|
| | Temperature | Pressure | VVH | H₂O/TOLUENE | | | |
| XII | 442° C. | 2 bars | 0.90 | 8 | 50 h | 92.7% | 82.5% |
| XIII | 430° C. | 2 bars | 1.45 | 5.4 | 6 h | 64.1% | 88.5% |
| | — | — | — | — | 24 h | 61.9% | 89.5% |
| | — | — | — | — | 50 h | 59.1% | 91.0% |
| | — | — | — | — | 200 h | 54.8% | 92.2% |
| XIV | 400° C. | 6 bars | 0.90 | 8 | 6 h | 57.0% | 90% |
| | — | — | — | — | 24 h | 53.2% | 91.5% |
| | — | — | — | — | 50 h | 51.1% | 92.5% |
| | — | — | — | — | 200 h | 50.9% | 92.8% |
| XV | 400° C. | 41 bars | 0.90 | 8 | 6 h | 54.1% | 91% |
| | — | — | — | — | 24 h | 53.0% | 92% |
| | — | — | — | — | 50 h | 53.0% | 92.5% |
| | — | — | — | — | 200 h | 52.8% | 92.5% |

TABLE VII

| EX. | Catalyst No. | % Metals | | Test Conditions | | | | 6 hours | | 24 hours | |
|---|---|---|---|---|---|---|---|---|---|---|---|
| | | | | Temp. | Pressure | VVH | H₂O/TOL. | Conversion | Selectivity | Conversion | Selectivity |
| XVI | 7 | 0.5%Rh | 0.1%Ir | 405° C. | 2 bars | 0.9 | 8 | 52% | 91% | 48.5% | 93.5% |
| XVII | 8 | 0.5%Rh | 0.1%Pt | 405° C. | 2 bars | 0.9 | 8 | 51% | 92% | 45% | 95.5% |
| XVIII | 9 | 0.5%Rh | 0.1%Pd | 405° C. | 2 bars | 0.9 | 8 | 51% | 92% | 45.5% | 95.5% |
| XIX | 6 | 0.6%Rh | | 405° C. | 2 bars | 0.9 | 8 | 55% | 89.5% | 52.5% | 90.5% |

TABLE VIII

| EXAMPLE | CATALYST | COMPOSITION | Test Conditions | | | | Results At 50 Hours | |
|---|---|---|---|---|---|---|---|---|
| | | | Temp. | Pressure | VVH | H₂O/TO. | Conversion | Selectivity |
| XX | 10 | 0.6% Rh on Ni₀.₇₅Mn₀.₂₅Al₂O₄ | 426° C. | 2 bars | 0.9 | 8 | 69.5% | 89.5% |
| XXI | 11 | 0.6% Rh on Ni₀.₇₅Cu₀.₂₅Al₂O₄ | 426° C. | 2 bars | 0.9 | 8 | 64.5% | 90% |
| XXII | 12 | 0.6% Rh on Ni₀.₇₅Zn₀.₂₅Al₂O₄ | 426° C. | 2 bars | 0.9 | 8 | 65.5% | 90% |
| XI (rap.) | 6 | 0.6% Rh on Ni₀.₇₅Mg₀.₂₅Al₂O₄ | 426° C. | 2 bars | 0.9 | 8 | 70.9% | 89.0% |

What is claimed is:

1. In a water dealkylation catalyst for petroleum fractions containing monoalkylated or polyalkylated aromatic hydrocarbons including at least one metal of group VIII deposited in a proportion of from 0.1 to 5% by weight on a spinel having improved activity, selectivity and stability, the improvement which comprises a carrier of mixed spinel of the formula $(M_xM'_{1-x})Al_2O_4$ wherein M is a bivalent base metal of group VIII of the Periodic Table, M' is a bivalent metal selected from groups 2a, 7b, 1b and 2b of the Periodic Table, wherein the molar ratio M/M' is from about 0.5:1 to 50:1 and wherein x is the molar fraction of M.

2. A catalyst of claim 1, wherein M is selected from the group consisting of nickel, iron, cobalt and mixtures thereof.

3. A catalyst of claim 1, wherein M' is selected from the group consisting of magnesium, manganese, copper, zinc and mixtures thereof.

4. A catalyst of claim 1, wherein M is selected from the group consisting of nickel, iron, cobalt and mixtures thereof and M' is selected from the group consisting of magnesium, manganese, copper, zinc and mixtures thereof.

5. A catalyst of claims 1, 2 or 3, wherein the group VIII supported on said spinel is a metal selected from the group consisting of rhodium, platinum, palladium, iridium and mixtures thereof.

6. The catalyst of claim 1, 2 or 3, wherein the group VIII metal supported on said spinel is selected from the group consisting of rhodium, iridium and mixtures thereof.

7. The catalyst of claim 4, wherein the group VIII metal supported on the spinel is selected from the group consisting of rhodium, platinum, palladium, iridium and mixtures thereof.

8. A catalyst according to claim 1, 4 or 7, wherein at least one metal of group VIII is deposited on the mixed spinel by impregnation with aqueous solutions of salts of the metals selected, and the carrier thus impregnated is dried, calcined in the air, reduced prior to use in a current of hydrogen at a temperature of 400° to 550° C. and treated by a current of water vapor at a temperature of 400° to 600° C. for from 5 minutes to 15 hours.

9. A catalyst of claim 1, 4 or 7, wherein the mixed spinel is a spinel $(Ni_xMg_{1-x}) Al_2O_4$ wherein the Ni/Mg ratio is from 1:1 to 3:1.

10. A catalyst of claim 1, wherein the mixed spinel is a spinel $(Ni_{0.75}Mg_{0.25}) Al_2O_4$.

11. A catalyst of claim 3, wherein the spinel is selected from the group consisting of $(Ni_{0.75}Mn_{0.25}) Al_2O_4$—$(Ni_{0.75}Cu_{0.25}) Al_2O_4$ and $(Ni_{0.75}Zn_{0.25}) Al_2O_4$.

12. A catalyst of claim 5 comprising a mixture of 2 metals of group VIII on a mixed spinel, the relative proportion of said 2 metals being from 1/10 to 10/1.

13. A catalyst according to claim 2 wherein the molar ratio M/M' is between 1 and 20.

* * * * *

UNITED STATES PATENT AND TRADEMARK OFFICE
CERTIFICATE OF CORRECTION

PATENT NO. : 4,233,186

DATED : November 11, 1980

INVENTOR(S) : Daniel Duprez, et al

It is certified that error appears in the above—identified patent and that said Letters Patent is hereby corrected as shown below:

Column 1, lines 27-28: Change "cerium or uranium. French Pat. No. 2,169,875 to UOP described" to --cerium or uranium in their French Pat. No. 2,169,875. UOP described--.

line 30: After "3,436,433" insert --)--.

line 64: Change "spatial speed" to --space velocity--.

Column 3, line 60: Change "II to IV" to --II to V--.

Column 4, line 21: Change "9 h" to --90 h--.

line 56: Change "XVII TO XIX" to --XVI TO XIX--.

line 59: Change "o" to --on--.

Column 6, Table I, top line, last column: "25 h" should be --24 h--.

Columns 5-6, Table II: After the third line of the last four columns, respectively, insert the following across the line:

-- 50 h      76%      77%      0.585 --.

UNITED STATES PATENT AND TRADEMARK OFFICE
CERTIFICATE OF CORRECTION

PATENT NO. : 4,233,186
DATED : November 11, 1980
INVENTOR(S) : Daniel Duprez, et al It is certified that error appears in the above—identified patent and that said Letters Patent is hereby corrected as shown below:

Column 6, Table III, fourth line of the last two columns:
"81%" should read --78%--; in last column insert --81%--.

Column 4, after line 2: insert in the middle of the line, as the title, -- EXAMPLE VI --.

Signed and Sealed this

Twenty-eighth Day of April 1981

[SEAL]

Attest:

RENE D. TEGTMEYER

Attesting Officer

Acting Commissioner of Patents and Trademarks